(12) United States Patent
Matsuoka et al.

(10) Patent No.: US 10,018,586 B2
(45) Date of Patent: Jul. 10, 2018

(54) ELECTROCHEMICAL MEASUREMENT DEVICE

(71) Applicant: HITACHI HIGH-TECHNOLOGIES CORPORATION, Tokyo (JP)

(72) Inventors: Shinya Matsuoka, Tokyo (JP); So Oguchi, Tokyo (JP); Yukie Tokiwa, Tokyo (JP); Toshinari Sakurai, Tokyo (JP); Yasushi Niiyama, Tokyo (JP); Noriko Iizumi, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 321 days.

(21) Appl. No.: 14/760,032

(22) PCT Filed: Jan. 14, 2014

(86) PCT No.: PCT/JP2014/050393
§ 371 (c)(1),
(2) Date: Jul. 9, 2015

(87) PCT Pub. No.: WO2014/115591
PCT Pub. Date: Jul. 31, 2014

(65) Prior Publication Data
US 2015/0355140 A1 Dec. 10, 2015

(30) Foreign Application Priority Data

Jan. 23, 2013 (JP) .................................. 2013-009733

(51) Int. Cl.
*G01N 27/416* (2006.01)
(52) U.S. Cl.
CPC ................................ *G01N 27/4163* (2013.01)

(58) Field of Classification Search
CPC ..................................... G01N 27/416–27/4163
See application file for complete search history.

(56) References Cited

U.S. PATENT DOCUMENTS

| 5,288,387 A | 2/1994 | Ito et al. |
| 5,620,579 A * | 4/1997 | Genshaw ............... C12Q 1/004 |
| | | 204/402 |

(Continued)

FOREIGN PATENT DOCUMENTS

| EP | 0859228 A2 | 8/1998 |
| JP | 61-031951 A | 2/1986 |

(Continued)

OTHER PUBLICATIONS

International Search Report of PCT/JP2014/050393.

*Primary Examiner* — J. Christopher Ball
(74) *Attorney, Agent, or Firm* — Mattingly & Malur, PC

(57) ABSTRACT

A flow cell for electrochemical measurement which introduces a sample solution, applies a voltage between a working electrode and a counter electrode to analyze the sample solution electrochemically, discharges the sample solution, and performs the electrochemical measurement continuously. The flow cell includes a unit which measures a value of a current flowing between electrodes at the time of applying a voltage, a unit which records the measured current value, a unit which compares the recorded current value with a current value set separately as a determination standard, and a unit which determines whether the current value measured at a cycle of a determination target and the recorded current value is normal by the comparison.

9 Claims, 6 Drawing Sheets

(56) References Cited

U.S. PATENT DOCUMENTS

2008/0173552 A1* 7/2008 Wu .................... A61B 5/14532
                                                        205/775
2009/0119047 A1* 5/2009 Zelin ........................ G01K 3/04
                                                        702/82

FOREIGN PATENT DOCUMENTS

| | | |
|---|---|---|
| JP | 62-156553 A | 7/1987 |
| JP | 63-173950 A | 7/1988 |
| JP | 4-230841 A | 8/1992 |
| JP | 06-109687 A | 4/1994 |
| JP | 10-288592 A | 10/1998 |
| JP | 11-083801 A | 3/1999 |

* cited by examiner

FIG. 3

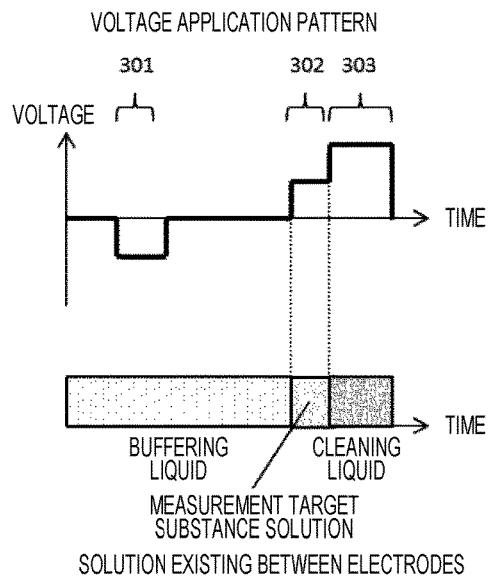

VOLTAGE APPLICATION PATTERN 301   302 303

VOLTAGE → TIME

SOLUTION EXISTING BETWEEN ELECTRODES
BUFFERING LIQUID | MEASUREMENT TARGET SUBSTANCE SOLUTION | CLEANING LIQUID → TIME

FIG. 4

MEASUREMENT VALUE LIST

| No | ITEM | MEASUREMENT DATE AND TIME | MEASUREMENT VALUE | NOTE |
|----|------|---------------------------|-------------------|------|
| 1 | A | 2012/11/10 08:50 | 2,152 | |
| 2 | A | 2012/11/10 08:51 | 2,258 | |
| 3 | B | 2012/11/10 08:52 | 5,552 | |
| 4 | B | 2012/11/10 08:53 | 5,145 | |
| 5 | B | 2012/11/10 08:54 | 4,750 | *CURRENT ABNORMALITY |
| 6 | B | 2012/11/10 08:55 | 5,874 | |
| 7 | A | 2012/11/10 08:56 | 2,087 | |
| 8 | A | 2012/11/10 08:57 | 2,658 | |
| 9 | C | 2012/11/10 08:58 | 258 | |
| 10 | C | 2012/11/10 08:59 | 148 | |

ALARM INFORMATION

No. 5    ALARM CONTENT
         CURRENT ABNORMALITY
         CURRENT VALUE OF PRESENT MEASUREMENT IS GREATLY DIFFERENT FROM CURRENT VALUES OF OTHER MEASUREMENTS AS RESULT OF COMPARISON. PLEASE EXAMINE PROPRIETY OF MEASUREMENT RESULT CAREFULLY.

FIG. 5

EXAMPLE 1a

|  | CURRENT | | |
|---|---|---|---|
|  | AFTER 0.1 SECONDS | AFTER 0.2 SECONDS | AFTER 0.3 SECONDS |
| DETERMINATION TARGET CYCLE | 5.2 | 7.4 | 9.2 |
| BEFORE ONE CYCLE | 5.1 | 7.5 | 9.2 |
| BEFORE TWO CYCLES | 5.2 | 7.4 | 9.2 |
| BEFORE THREE CYCLES | 5.2 | 7.5 | 9.2 |
| AVERAGE | 5.2 | 7.5 | 9.2 |
| DIFFERENCE | 0 | 0.1 | 0 |
| PROPRIETY DETERMINATION |  | NORMAL |  |

EXAMPLE 1b

|  | CURRENT | | |
|---|---|---|---|
|  | AFTER 0.1 SECONDS | AFTER 0.2 SECONDS | AFTER 0.3 SECONDS |
| DETERMINATION TARGET CYCLE | 4.5 | 4.6 | 4.8 |
| BEFORE ONE CYCLE | 5.1 | 7.5 | 9.2 |
| BEFORE TWO CYCLES | 5.2 | 7.4 | 9.2 |
| BEFORE THREE CYCLES | 5.2 | 7.5 | 9.2 |
| AVERAGE | 5.2 | 7.5 | 9.2 |
| DIFFERENCE | -0.7 | -2.9 | -4.4 |
| PROPRIETY DETERMINATION |  | ABNORMAL |  |

EXAMPLE 2

|  | CURRENT | | |
|---|---|---|---|
|  | AFTER 0.1 SECONDS | AFTER 0.2 SECONDS | AFTER 0.3 SECONDS |
| DETERMINATION TARGET CYCLE | 4.5 | 7.4 | 9.2 |
| BEFORE ONE CYCLE | 4.6 | 7.5 | 9.2 |
| BEFORE TWO CYCLES | 4.6 | 7.4 | 9.2 |
| BEFORE THREE CYCLES | 4.6 | 7.5 | 9.2 |
| AVERAGE | 4.6 | 7.5 | 9.2 |
| DIFFERENCE | -0.1 | 0.1 | 0 |
| PROPRIETY DETERMINATION |  | NORMAL |  |

FIG. 6

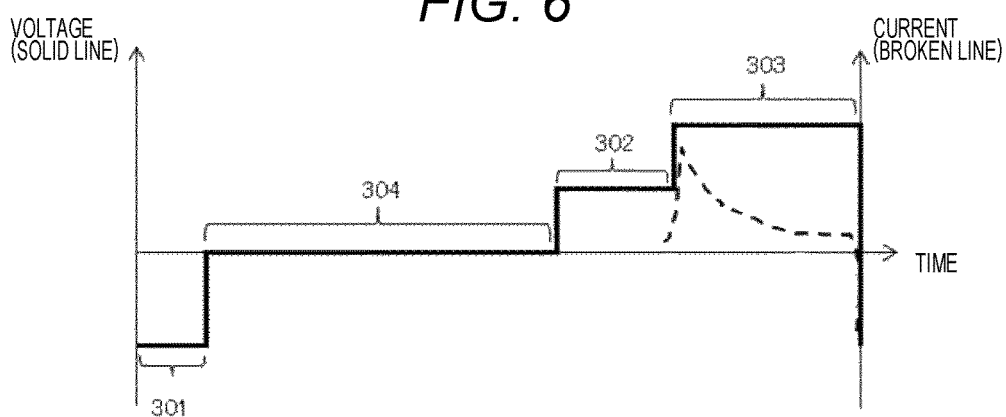

FIG. 7

| CYCLE COUNT NUMBER | SPECIFIC CURRENT VALUE |
|---|---|
| 1 | 28.2 |
| 2 | 37.7 |
| 3 | 21.6 |
| 4 | 19.7 |
| 5 | 18.4 |
| 6 | 16.7 |
| 7 | 16.3 |
| 8 | 16.3 |
| 9 | 16.3 |
| 10 | 16.4 |
| ⋮ | ⋮ |
| 52001 | 17.2 |
| 52002 | 17.3 |
| 52003 | 17.2 |
| 52004 | 17.4 |
| 52005 | 17.6 |
| 52006 | 17.7 |
| 52007 | 17.9 |
| 52008 | 18.3 |
| 52009 | 18.9 |
| 52010 | 19.2 |
| 52011 | 19.2 |

DETERMINATION RESULT

DETERMINATION  B

PLEASE REFER TO FOLLOWING DETERMINATION TABLE FOR DETAILS.

| | |
|---|---|
| A | RECOMMEND THAT ELECTROCHEMICAL FLOW CELL IS EXCHANGED IN TWO WEEKS TO ONE MONTH. PLEASE CONTACT SERVICE MANAGER, IF NECESSARY. |
| B | RECOMMEND THAT ELECTROCHEMICAL FLOW CELL IS EXCHANGED IN ONE MONTH TO THREE MONTHS. PLEASE CONTACT SERVICE MANAGER, IF NECESSARY. |
| C | RECOMMEND THAT ELECTROCHEMICAL FLOW CELL IS EXCHANGED IN THREE MONTHS TO TWELVE MONTHS. PLEASE CONTACT SERVICE MANAGER, IF NECESSARY. |

ELECTROCHEMICAL MEASUREMENT DEVICE

TECHNICAL FIELD

The present invention relates to an electrochemical measurement device that performs electrochemical measurement using a flow cell.

BACKGROUND ART

Electrochemical measurement means a method of measuring properties of chemical substances electrically. As an example of a measuring instrument to perform the electrochemical measurement, an electrochemical measurement flow cell disclosed in PTL 1 is known. The electrochemical measurement flow cell has a structure in which a flow channel is provided in a body having chemical resistance such as PEEK and electrodes are arranged to contact the flow channel and is mainly used as a detector of liquid chromatography or flow injection analysis.

In the electrochemical measurement flow cell, a solution containing a measurement target substance is introduced into the flow channel and measurement is performed. After the measurement, appropriate cleaning is performed and the electrochemical measurement flow cell is repetitively used. The electrodes used for the electrochemical measurement generally include three kinds of electrodes to be a working electrode, a counter electrode, and a reference electrode. For the working electrode and the counter electrode among these electrodes, stable metals such as platinum are used to prevent the electrodes from affecting a reaction of the measurement target. The reference electrode is an electrode having a special function of maintaining a potential constantly and a silver/silver chloride electrode is used as the reference electrode.

The electrochemical measurement flow cell is generally used for the repetitive measurement after the appropriate cleaning. Because the electrochemical measurement flow cell has a relatively complicated structure with the electrodes and the flow channel, it is not preferable to use the electrochemical measurement flow cell as a disposable product, from the viewpoint of a cost and maintenance. As the electrochemical measurement flow cell is repetitively used, a measurement value may be changed due to a change of an electrode property, a change of a flow channel structure, and contamination of an inner portion of the flow cell. In addition, the measurement value may not be correctly obtained due to unexpected events such as adhesion of a chemical substance to an electrode surface, mixture of air bubbles in the flow channel, and damages of the electrodes. As described above, in the abnormal case, it may be predicted that a current flowing between the electrodes changes as compared with the normal case, the abnormality may be detected by monitoring a current value, and the possibility of incorrect measurement may be communicated.

CITATION LIST

Patent Literature

PTL 1: JP 6-109687 A

SUMMARY OF INVENTION

Technical Problem

A value of a current flowing between the electrodes at the time of applying a voltage in the electrochemical measurement flow cell may not be necessarily the same value by an individual difference of such as the electrochemical measurement flow cell, the measurement device, and the measurement target solution or a combination thereof. For this reason, it is difficult to determine a constant threshold value common to all flow cells and detect the possibility of measurement abnormality by a comparison with the threshold value.

Solution to Problem

A main characteristic of the present invention is that an electrochemical measurement device performing measurement using a flow cell for electrochemical measurement which introduces a sample solution, applies a voltage between a working electrode and a counter electrode to analyze the sample solution electrochemically, discharges the sample solution, and performs the electrochemical measurement continuously, the electrochemical measurement device includes: a control device including a current measurement unit which measures a value of a current flowing between electrodes at the time of applying a voltage, a storage unit which records the measured current value, a comparison unit which compares a current value measured at a cycle of a measurement target with a determination standard based on a current value obtained at a cycle before the cycle and stored in the storage unit, and a determination unit which determines whether the current value measured at the cycle of the measurement target is normal by the comparison unit; and a communication device which, when it is determined that the measured current value is not normal, communicates abnormality of the current value to an operator.

Advantageous Effects of Invention

According to the invention, it is possible to decrease the possibility of incorrect analysis due to an abnormal electrode state or an abnormal flow channel state caused by any factor in continuous measurement using an electrochemical measurement flow cell.

BRIEF DESCRIPTION OF DRAWINGS

FIG. 3 is a diagram illustrating a measurement cycle.

FIG. 4 is a diagram illustrating a screen to communicate the possibility of measurement abnormality.

FIG. 5 is a diagram illustrating an example of the case in which current values at a determination target cycle and cycles before the determination target cycle are compared and propriety is determined.

FIG. 6 is a diagram illustrating a measurement cycle and an applied voltage and a generated current value.

FIG. 7 is a diagram illustrating an example of the case in which a measurement cycle number of an electrochemical measurement flow cell and a current value are compared and an exchange time is determined.

FIG. 8 is a diagram illustrating an example of the case in which a category showing an exchange time of an electrochemical measurement flow cell predicted from an error rate is communicated to a user or a manager of an electrochemical measurement device.

DESCRIPTION OF EMBODIMENTS

Figure 1:
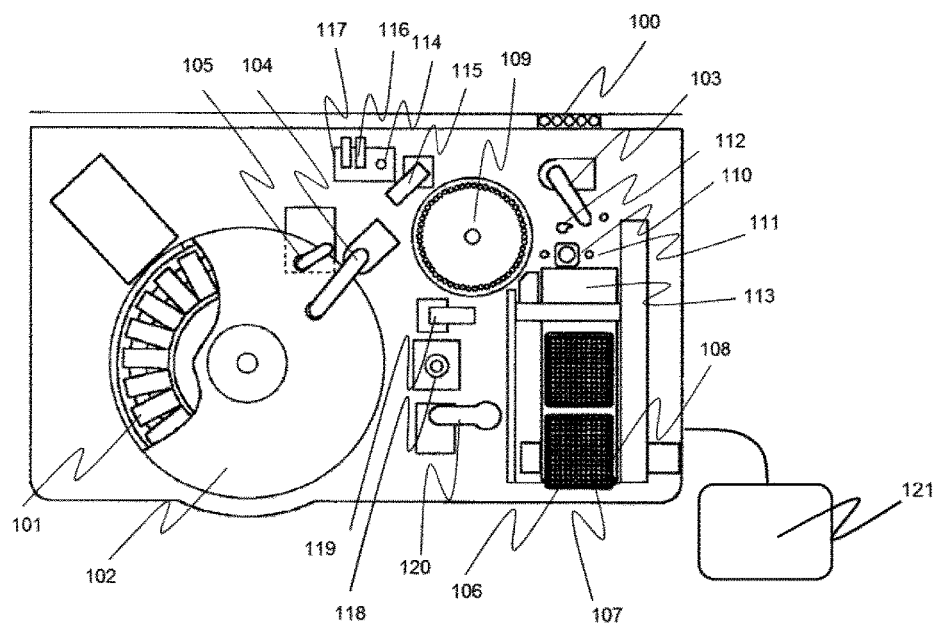
FIG. 1 is a diagram illustrating an electrochemical measurement flow cell and a measurement device to which the present invention is applied.

First, an electrochemical measurement flow cell and a measurement device to which the present invention is applied will be described using FIG. 1.

An automatic immunological analyzer includes a sample rack 100 to load a sample, a reagent disk 102 to store a reagent vessel 101, a sample dispensation mechanism 103 to fractionate/dispense the sample, a reagent dispensation mechanism 104 to fractionate/dispense reagents, a magnetic particle stirring mechanism 105 to stir a magnetic particle solution among the reagents, a reaction vessel 106 to put the fractionated sample and reagent and perform a reaction, a disposable dispensation chip 107 to be attached to a tip of the sample dispensation mechanism and to be used when the sample is fractionated/dispensed, a magazine 108 to store the reaction vessel and the dispensation chip, an incubator 109 to load the reagent and sample dispensed reaction vessel, maintain a temperature constantly, and perform the reaction, a conveyance mechanism 113 to convey the reaction vessel to the incubator and a reaction vessel disposing unit 110 and convey the dispensation chip to a dispensation chip mounting position 111 and a dispensation chip disposing place 112, a conveyance mechanism 115 for BF separation to convey the reaction vessel from the incubator to a magnetic separation unit 114, a reaction solution suction mechanism 116 to suck a reaction solution from the reaction vessel conveyed to the magnetic separation unit, a cleaning liquid ejection mechanism 117 to eject a cleaning liquid to the reaction vessel conveyed to the magnetic separation unit, a detecting unit conveyance mechanism 119 to convey the reaction vessel from the incubator to a detecting unit 118 or from the detecting unit to the incubator, and a detection reagent ejection mechanism 120 to eject a reagent for detection to the reaction vessel conveyed to the detecting unit. The electrochemical flow cell described in the present invention is mounted in a detector. Individual functions of controlling a voltage, measuring a current, recording a measured current, comparing a current value with a current value used as a determination standard, setting the current value used as the determination standard, and determining whether the current value is normal, which are described below, are realized by a microcomputer 121. The microcomputer 121 has functions of controlling an application voltage control unit, a current measurement unit, a current recording unit, a comparison unit with the determination standard, and a determination standard setting unit and determining whether the measured current value is normal.

Figure 2:
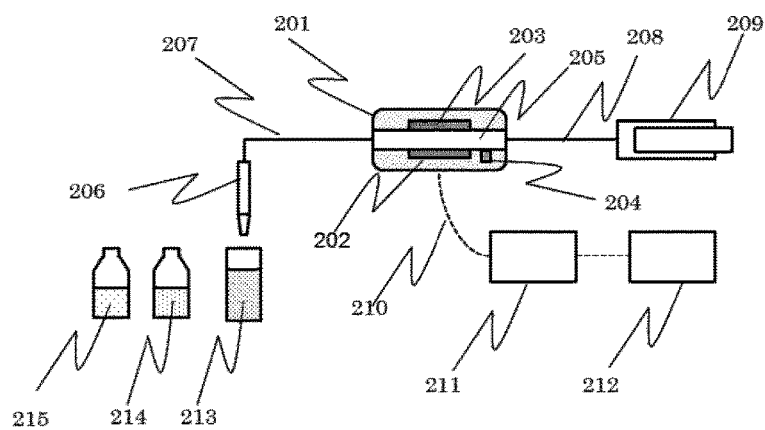
FIG. 2 is a diagram illustrating an electrochemical flow cell and a measurement system using the same.

Next, an electrochemical measurement flow cell portion will be described in detail using FIG. 2.

In an electrochemical measurement flow cell 201, three kinds of electrodes including a working electrode 202, a counter electrode 203, and a reference electrode 204 are arranged to face a flow channel 205. Here, a platinum electrode is used as the working electrode and the counter electrode and a silver/silver chloride electrode is used as the reference electrode. The electrochemical measurement flow cell and a nozzle 206 for solution suction are connected by an external flow channel 207 such as a tube. An external flow channel 208 is attached to the side of an outlet of the electrochemical measurement flow cell and a solution driving unit 209 such as a syringe pump is connected to a front portion thereof. A wiring line 210 is extracted from the three kinds of electrodes of the electrochemical measurement flow cell and the wiring line is connected to a voltage application/current measurement unit 211. The voltage application/current measurement unit is configured by a voltage control device such as a potentiostat and a power supply, for example. In the voltage application/current measurement unit, control of an application voltage and measurement of a current are performed by a control/operation/recording unit 212 realized by a computer and a computer program. In addition, current measurement values corresponding to a plurality of cycles needed in the present invention are recorded and operated by the control/operation/recording unit. The nozzle is driven in vertical and horizontal directions by a nozzle driving mechanism not illustrated in the drawings and can suck each of a solution 213 containing a measurement target substance, a cleaning liquid 214, and a buffering solution 215. The electrochemical measurement is repetitively performed including cleaning by the cleaning liquid while a plurality of measurement target substance solutions is measured.

Next, the electrochemical measurement performed in the electrochemical measurement flow cell will be described using FIG. 3. In FIG. 3, a horizontal axis shows a time in a cycle and a vertical axis shows an application voltage of the working electrode for the reference electrode. For the same horizontal axis and time, kinds of liquids existing between the working electrode and the counter electrode at timing thereof are illustrated.

First, at timing shown by 301, a buffering liquid is filled between the electrodes, a negative voltage is applied for 0.3 seconds, and an oxide film generated on a surface of the platinum electrode of the working electrode is removed. This process is called conditioning. Then, at a timing shown by 304, no voltage is applied to the electrodes. Next, at timing shown by 302, a solution containing the measurement target substance is introduced between the electrodes, a positive voltage is applied to the working electrode for 1.4 seconds, and a current flowing at that time is measured. Because the flown current is proportional to an amount of the measurement target substance, the amount of the measurement target substance can be determined by measuring the current. This process is called the electrochemical measurement. Next, at timing shown by 303, a voltage higher than the voltage at the time of the electrochemical measurement is applied for 3.0 seconds in a state in which the cleaning liquid is filled between the electrodes and the measurement target substances remaining on the surfaces of the electrodes are removed. This process is called cleaning. A series of measurement manipulations described above is called a cycle.

First Embodiment

A method of determining propriety of an electrode state according to a first embodiment of the present invention will be described.

At the time of the conditioning, the oxide film is removed as a voltage application time passes and a current flowing between the electrodes increases. Voltages after 0.1, 0.2 and 0.3 seconds pass from application of a conditioning voltage are measured and recorded. At the time of the conditioning, if there is no large change in an electrode state, the current does not generally change greatly during several cycles.

Therefore, it is determined that, when a current at a determination target cycle is compared with an average of currents at one cycle to three cycles before the determination target cycle and a difference of a predetermined threshold value, here, ±0.5 mA or more exists, the electrode state is abnormal.

When the electrode state is not normal, an amount determination result is not obtained normally and an erroneous result may be communicated. In this case, an alarm showing "abnormality of a current value is detected and measurement may not be correctly performed" is added to the result to urge a user to examine the measurement result carefully.

FIG. 4 illustrates an example of a communication method for the user. Here, it is assumed that current abnormality is detected by a method described in the present patent in fifth measurement, using the case in which a series of measurement results is displayed in a form of a list as an example. In a field of a note of a measurement result display portion of No. 5 in a measurement value list, "* current abnormality" is displayed. In addition, occurrence of "current abnormality" in the measurement of No. 5 and details of the abnormality and calling attention for the measurement result are displayed in a different field of alarm information. Thereby, the user can know that the result may include a measurement error and can take a necessary countermeasure such as remeasurement and comparison with other measurement value.

Next, a specific determination method will be described using FIG. 5. FIG. 5 illustrates currents after 0.1 seconds, 0.2 seconds, and 0.3 seconds pass from a voltage application start at a determination target cycle, one cycle before the determination target cycle, two cycles before the determination target cycle, and three cycles before the determination target cycle. In addition, an average value of the currents corresponding to the three cycles at each timing is illustrated. A difference of the current value of the determination target cycle and the average value is computed, the difference is compared with the predetermined threshold value, and propriety of the determination target cycle is determined.

In an example 1a of FIG. 5, at any timing after 0.1 seconds, 0.2 seconds, and 0.3 seconds, because the difference of the current at the determination target cycle and the average of the currents at one cycle, two cycles, and three cycles before the determination target cycle is equal to or smaller than 0.5 mA to be the threshold value, it is determined that there is no abnormality in the current value. Meanwhile, in an example 1b of FIG. 5, the current value at the determination target cycle decreases as compared with the current values at the cycles before the determination target cycle. For example, after 0.1 seconds, a difference with the average is 0.7 mA and is more than 0.5 mA to be the threshold value and thus, it is determined that there is the current abnormality at the determination target cycle.

In an example 2 of FIG. 5, the case in which a current value measured by a combination of a different electrochemical measurement flow cell and a measurement device decreases as compared with the case of the example 1 is assumed. In this case, at the determination target cycle, the same value as the value determined as the abnormality in the example 1b, that is, 4.5 mA is detected. However, an average of current values at three cycles before the determination target cycle is 4.7 mA and a difference of the current value at the determination target cycle and the average value is 0.2 mA. Because the difference is smaller than 0.5 mA to be the threshold value, it is determined that the determination target cycle is normal in the case of the example 2. By applying the present invention, appropriate propriety determination is enabled without erroneously determining the case illustrated in the example 2 as the abnormality.

Here, it is necessary to use at least one point during application of a voltage when the electrode state is determined. Here, three points (after 0.1 seconds, after 0.2 seconds, and after 0.3 seconds) are used. However, more points can be used. More points are used, so that the possibility of erroneously determining abnormality of a current value not including measurement abnormality occurred accidentally by electrical noise can be decreased. In actuality, when the current value becomes abnormal due to the abnormality of the measurement, it is predicted that values different from values in a normal state are obtained at all of a plurality of measurement points. Meanwhile, when only one point is used and an abnormal current value is accidentally measured at a measurement point thereof, the measurement may be determined as the abnormality. The normality or the abnormality of the measurement can be determined by recognizing patterns of waveforms using all of the points at which the current has been measured.

In addition, the three cycles before the determination target cycle are used as the cycles to calculate the reference value to determine the propriety of the electrode state at the determination target cycle. However, only the cycle immediately before the determination target cycle can be used or more cycles can be used. Even in any case, a determination method is the same as the method described herein.

When a temporal change of the current value is small to a degree to which the temporal change can be ignored, the threshold value used for the determination can be calculated from the value measured immediately after the electrochemical measurement flow cell is mounted in the device. In this case, the threshold value based on the previous measurement current value does not need to be calculated for each measurement while the same electrochemical measurement flow cell is continuously used and an operation can be simplified.

Second Embodiment

A second embodiment of the present invention will be described.

In this embodiment, a method of predicting an exchange time of an electrochemical measurement flow cell using the phenomenon of a current value or a voltage value at timing of application of a constant voltage increasing or decreasing continuously according to an ordinal scale will be described. According to an effect of this embodiment, a user or a manager of an electrochemical measurement device can easily obtain a prospect of an action plan other than preventive maintenance and a periodic exchange.

In a cleaning process 303, if a positive voltage is applied to electrodes, an oxide film of surfaces of the electrodes is removed and a positive current value is generated between the electrodes. The current value is generated continuously during application of the positive voltage in the cleaning process while being converged after generating a large positive value in synchronization with the application of the positive voltage in the cleaning process. An example of a waveform of the obtained current value is shown by a broken line in FIG. 6. The current value generated in the cleaning process generally shows a stable value even when cycles are different. However, a minute change in the current value may be accepted as the electrochemical measurement flow cell is continuously used. Among the current values generated at the time of the cleaning process, a generation time of the current value in which a change for each cycle is easily confirmed is set as a specific time and the current value generated in the specific time is set as a specific current value. In this embodiment, 0.5 seconds after the voltage application in the cleaning process are sets the specific time, the current value obtained at the timing is defined as the specific current value, the current value is measured by a current value measurement unit 403 for each cycle, the current value is accumulated by a control/operation/recording unit 212, and a statistical operation process is executed.

When the statistical operation process is executed on the specific current value generated by the cleaning process at any continuous cycle and the specific current value increases or decreases continuously according to a predetermined ordinal scale, it can be determined that an electrode state changes temporally and the exchange time of the electrochemical measurement flow cell can be predicted. The prediction of the exchange time of the electrochemical measurement flow cell can be performed by a combination with the number of cycles used by the electrochemical measurement flow cell.

Next, the ordinal scale to detect a temporal change of the electrodes will be described. The ordinal scale is set by accumulating current value information whenever a cycle is repeated from a first cycle at which continuous measurement is performed by the electrochemical measurement flow cell. For example, in an initial period of a use start, a specific current value at timing where a change in the current value is largest is used for each cycle. In this embodiment, a threshold value of the continuous number of times of the specific current value determined by the ordinal scale is defined as 7 and is set to an automatic immunological analyzer to which a control/operation/recording unit 212 is connected through an input unit 402.

A voltage application/current measurement unit is controlled by the control/operation/recording unit 212 realized by a computer and a computer program and performs control of an application voltage and measurement of a current. In this embodiment, the control/operation/recording unit is used such that a measurement cycle number from timing immediately after the use start of the electrochemical measurement flow cell is counted and current value information accumulated for each measurement cycle and a count value of the measurement cycle number are accumulated or displayed.

Next, monitoring of the specific current value and counting of the measurement cycle number from the timing immediately after the use state of the electrochemical measurement flow cell to any measurement cycle number will be described using FIG. 7. In FIG. 7, a current value after 0.5 seconds pass from the start of the voltage application in the cleaning process is stored as an example of the specific current value in time series.

When the electrode state changes, the specific current value generated by the voltage application at the time of the cleaning process of the electrochemical flow cell is minute, but gradually increases or decreases. In this embodiment, for example, when the current value increases or decreases continuously at 7 cycles or more, it is determined that the flow cell needs to be exchanged. A current value from when the electrochemical measurement flow cell is mounted is monitored constantly by the control/operation/recording unit 212 and is displayed on a screen together with a count value of a cycle number to be an interval scale. As a result obtained by executing a statistical operation process on the specific measurement value according to the ordinal scale, when the specific measurement value increases or decreases continuously in the seven cycles or more, the cycles and the specific measurement value are extracted as a specific current value measurement feature 404 and are displayed for the user or the manager of the device.

Next, an alarm to communicate the exchange time of the electrochemical measurement flow cell and a determination method thereof will be described using FIG. 8.

Three categories of A, B, and C are previously provided for an error rate, in order of high exchange emergency of the electrochemical measurement flow cell. The categories may be provided to be set to the control/operation/recording feature 212 by the input unit 402.

An alarm of the category A is an alarm to be given when a specific current value increases or decreases continuously seven times or more and the electrochemical flow cell is used the predetermined number of times or more, as a minute error rate of the electrochemical measurement flow cell. In the case of corresponding to the category of the alarm A, information for recommending that the flow cell is exchanged in two weeks to one month is displayed.

An alarm of the category B is an alarm to be given when a specific current value increases or decreases continuously four times to six times and the electrochemical flow cell is used the predetermined number of times or more, as a minute error rate of the electrochemical measurement flow cell. In the case of corresponding to the category of the alarm B, information for recommending that the flow cell is exchanged in one month to three months is displayed.

An alarm of the category C is an alarm to be given when a variation of a specific current value increases or decreases continuously three times or less and the electrochemical flow cell is used the predetermined number of times or more, as a minute error rate of the electrochemical measurement flow cell. In the case of corresponding to the category of the alarm C, information for recommending that the flow cell is exchanged in three months to twelve months is displayed.

The alarms A to C are given before a start of a next cycle, when the continuous number of times of the specific current value determined by the previously set ordinal scale in the electrochemical measurement device is matched with any category. In addition, all of the generated alarms are stored in the control/operation/recording unit 212 of the electrochemical measurement device in ascending order or descending order of the count value of the measurement cycle number and are displayed on a display unit 401 according to necessity. In this embodiment, when the electrochemical measurement flow cell is used the predetermined number of times or more, the alarm is generated. However, when the electrochemical measurement flow cell is used in a predetermined period or more, the alarm may be generated.

Figure 9:
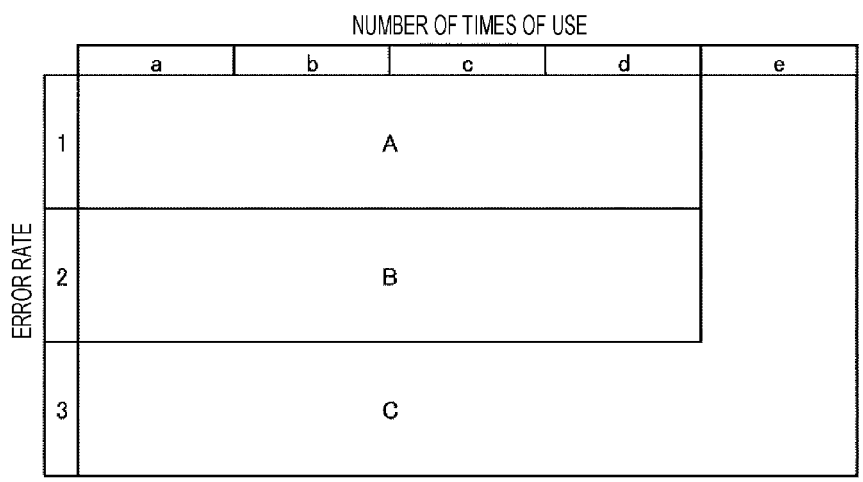
FIG. 9 is a diagram illustrating an example of the case in which the predictive probability of an exchange time of an electrochemical measurement flow cell is maximized.
Figure 10:
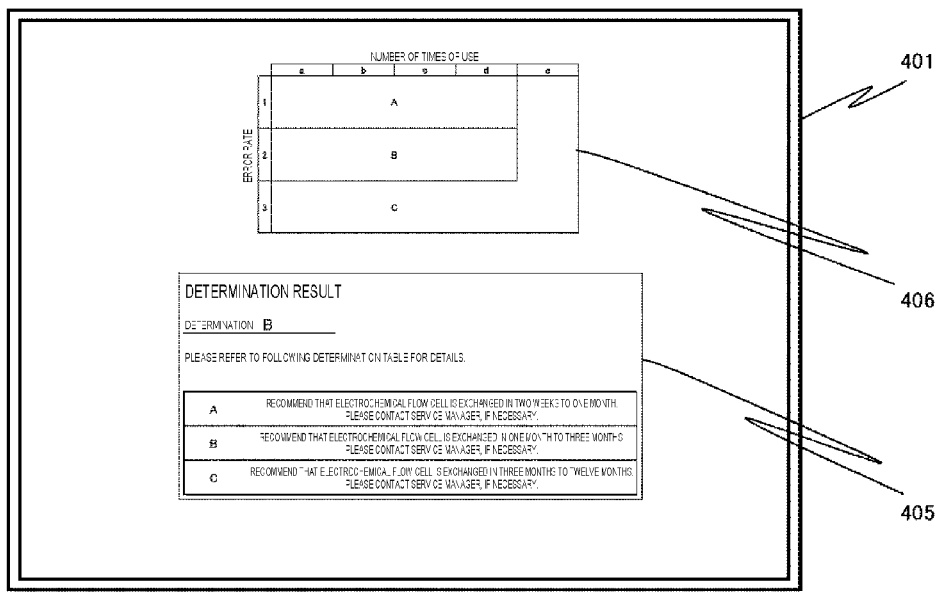
FIG. 10 is a diagram illustrating an example of the case in which an exchange time of an electrochemical measurement flow cell is displayed.

Next, a method of predicting the exchange time of the electrochemical measurement flow cell and communicating the exchange time to the user will be described using FIGS. 9 and 10.

The categories of the alarms A to C based on the minute change of the electrode property of the electrochemical measurement flow cell and the number of times of use of the electrochemical measurement flow cell are set to the control/operation/recording feature 212. In this embodiment, a predictive probability maximization feature 406 by a matrix correspondence format is used.

In the predictive probability maximization feature, it is determined whether the specific current value and the number of times of use monitored constantly by the control/operation/recording unit 212 correspond to the alarms A to C and the specific current value and the number of times of use are displayed on a display screen 401 according to necessity. FIG. 7 illustrates an example of the display screen. The minute error rate, the number of times of use of the electrochemical measurement flow cell, and the category may be set to the control/operation/recording unit 212 by an operator through the input unit 402 or may be changed.

In this embodiment, the cases in which occurrence numbers of a variation of the continuous increase or decrease of the specific current value are 1: not less than 7 times, 2: not less than 4 times and less than 7 times, and 3: less than 4 times are set as an error rate axis. An axis of the number of times of use is set in five steps of a to e on the basis of the number of times of use of the electrochemical flow cell. The number of times of use to distinguish each step can be arbitrarily set. The categories of A to C are set to corresponding matrixes on the basis of the error rate axis and the axis of the number of times of use and the exchange time predictive probability of the electrochemical measurement flow cell is maximized. Matrix display is illustrated in FIG. 9.

Alarm display is transmitted to the user or the manager of the electrochemical measurement device and the electrochemical measurement flow cell by an alarm display unit 405 through the display screen 401. An example of an alarm display screen is illustrated in FIG. 10. In the case of corresponding to any category, the alarm display screen displays category information on the display unit 401.

Figure 11:
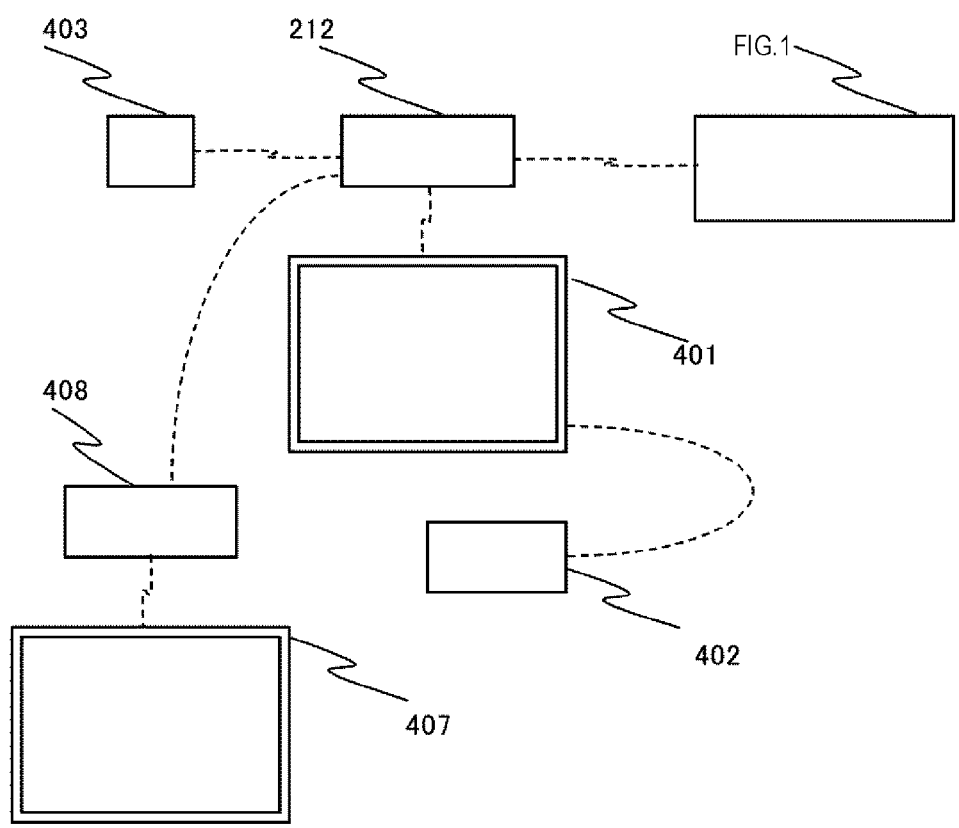
FIG. 11 is a diagram illustrating a relation of an electrochemical measurement flow cell, a measurement device, an input unit, and a display unit of an alarm.

In addition, alarm information may be stored as electronic information in the control/operation/recording unit 212 to be a non-display unit of the electrochemical measurement device, such that the user or the manager of the electrochemical measurement device can search the alarm information according to necessity. The electronic information may be output to an external display device 407 connected to the outside of a measurement device by the user or the manager of the electrochemical measurement device through a communication unit provided in the electrochemical measurement device, according to necessity, or may be output automatically and may be stored in an external recording unit 408. An example of a mutual relation of the measurement device, the control/operation/recording device 212, the display device 401, the input device 402, the current value measurement device 403, the external display device 407, and the external recording device 408 configured as described above is illustrated in FIG. 11.

According to this embodiment, the change tendency of the electrode can be detected in the continuous measurement using the electrochemical measurement flow cell.

REFERENCE SIGNS LIST 100 sample rack
101 reagent vessel
102 reagent disk
103 sample dispensation mechanism
104 reagent dispensation mechanism
105 particle stirring mechanism
106 reaction vessel
107 dispensation chip
108 magazine
109 incubator
110 reaction vessel disposing unit
111 dispensation chip mounting position
112 dispensation chip disposing place
113 conveyance mechanism
114 magnetic separation unit
115 conveyance mechanism for BF separation
116 reaction solution suction mechanism
117 cleaning liquid ejection mechanism
118 detecting unit
119 detecting unit conveyance mechanism
120 detection reagent ejection mechanism
121 microcomputer
201 electrochemical measurement flow cell
202 working electrode
203 counter electrode
204 reference electrode
205 flow channel
206 nozzle for solution suction
207 inlet-side external flow channel
208 outlet-side external flow channel
209 solution driving unit
210 wiring line
211 voltage application/current measurement unit
212 control/operation/recording unit
213 solution containing measurement target substance
214 cleaning liquid
215 buffering liquid
301 timing of conditioning
302 timing of electrochemical measurement
303 timing of cleaning

The invention claimed is:

1. An electrochemical measurement device comprising:
a flow cell for electrochemical measurement of a sample solution, the flow cell including a flow channel, a working electrode and a counter electrode; and
a control device connected to the flow cell and configured to control the flow cell to perform the electrochemical measurement by repeatedly performing a cycle, including a conditioning step including applying a first voltage between the working electrode and the counter electrode, an electrochemical measurement step including applying a second voltage between the working electrode and the counter electrode to analyze the sample solution in the flow cell, and a cleaning step including applying a third voltage between the working electrode and the counter electrode, as a plurality of cycles,
wherein the control device is further configured to:
measure, in the conditioning step, the electrochemical measurement step, or the cleaning step of a determination target cycle of the plurality of cycles, a current value of a current flowing between the working electrode and the counter electrode at the time of applying the first voltage, the second voltage, or the third voltage thereto;
record the measured current value;
compare the measured current value with a determination standard based on a current value obtained from the plurality of cycles which precede the determination target cycle including one of the plurality of cycles that occurred immediately before the determination target cycle; and
determine whether the measured current value is abnormal based on a result of the comparison; and
when the measured current value is abnormal, output an abnormality notification of the measured current value.

2. The electrochemical measurement device according to claim 1, wherein
the determination standard is a standard value based on the current value of a current flowing between the working electrode and the counter electrode at the time of applying the first voltage in the conditioning step, the second voltage in the electrochemical step, or the third voltage in the cleaning step of the plurality of cycles which precede the determination target cycle.

3. The electrochemical measurement device according to claim 1, wherein the control device is further configured to:
calculate the determination standard for each of the cycles.

4. The electrochemical measurement device according to claim 1, further comprising:
a display unit which displays the abnormality notification.

5. The electrochemical measurement device according to claim 1, wherein the control device is further configured to:
store current values measured in the conditioning step or the cleaning step associated with each of the cycles in time series after starting the electrochemical measurement in the flow cell, and
when the current values measured in the cycles are continuously increasing or decreasing a predetermined number of times or more as compared with the determination standard, output an alarm.

6. The electrochemical measurement device according to claim 5, wherein the control device is further configured to:
determine an electrode state of the working electrode and the counter electrode based on the current values measured in the cycles increasing or decreasing continuously, a number of times of use of the electrochemical flow cell, or a combination thereof.

7. The electrochemical measurement device according to claim 6, wherein the control device is further configured to:
output an exchange time for the electrochemical flow cell based on the electrode state.

8. An electrochemical measurement system, comprising:
an electrochemical measurement device;
a display device which is located remote from the electrochemical measurement device;
a control device which is located remote from the electrochemical measurement device and which is connected to the electrochemical measurement device and the display device,
wherein the electrochemical measurement device includes a flow cell for electrochemical measurement of a sample solution, the flow cell including a flow channel, a working electrode and a counter electrode,
wherein the control device is configured to control the flow cell to perform the electrochemical measurement by repeatedly performing a cycle, including a conditioning step including applying a first voltage between the working electrode and the counter electrode, an electrochemical measurement step including applying a second voltage between the working electrode and the counter electrode to analyze the sample solution in the flow cell, and a cleaning step including applying a third voltage between the working electrode and the counter electrode, as a plurality of cycles,
wherein the control device is further configured to:
measure, in the conditioning step, the electrochemical measurement step, or the cleaning step of a determination target cycle of the plurality of cycles, a current value of a current flowing between the working electrode and the counter electrode at the time of applying the first voltage, the second voltage, or the third voltage thereto;
record the measured current value;
compare the measured current value with a determination standard based on a current value obtained from the plurality of cycles which precede the determination target cycle including one of the plurality of cycles that occurred immediately before the determination target cycle; and
determine whether the measured current value is abnormal based on a result of the comparison; and
when the measured current value is abnormal, output an abnormality notification of the measured current value to the display device.

9. A method of detecting an abnormality in an electrochemical measurement device having a flow cell for electrochemical measurement of a sample solution, the flow cell including a flow channel, a working electrode and a counter electrode, the method comprising:
controlling the flow cell to perform the electrochemical measurement by repeatedly performing a cycle, including a conditioning step including applying a first voltage between the working electrode and the counter electrode, an electrochemical measurement step including applying a second voltage between the working electrode and the counter electrode to analyze the sample solution in the flow cell, and a cleaning step including applying a third voltage between the working electrode and the counter electrode, as a plurality of cycles;
measuring, in the conditioning step, the electrochemical measurement step, or the cleaning step of a determination target cycle of the plurality of cycles, a current value of a current flowing between the working electrode and the counter electrode at the time of applying the first voltage, the second voltage, or the third voltage thereto;
comparing the measured current value with a determination standard based on a current value obtained from the plurality of cycles which precede the determination target cycle including one of the plurality of cycles that occurred immediately before the determination target cycle;
determining whether the measured current value is abnormal based on a result of the comparison; and
when the measured current value is abnormal, outputting an abnormality notification of the measured current value.

* * * * *